US009289116B2

(12) United States Patent
Sato et al.

(10) Patent No.: US 9,289,116 B2
(45) Date of Patent: Mar. 22, 2016

(54) IMAGE PROCESSING APPARATUS AND IMAGE PROCESSING METHOD

(71) Applicant: CANON KABUSHIKI KAISHA, Tokyo (JP)

(72) Inventors: Makoto Sato, Tokyo (JP); Yoshihiko Iwase, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 150 days.

(21) Appl. No.: 14/065,906

(22) Filed: Oct. 29, 2013

(65) Prior Publication Data

US 2014/0119629 A1 May 1, 2014

(30) Foreign Application Priority Data

Oct. 30, 2012 (JP) ................................ 2012-239274
Jul. 31, 2013 (JP) ................................ 2013-159181

(51) Int. Cl.
*G06K 9/00* (2006.01)
*A61B 3/10* (2006.01)
*A61B 3/12* (2006.01)

(52) U.S. Cl.
CPC .. *A61B 3/102* (2013.01); *A61B 3/12* (2013.01)

(58) Field of Classification Search
None
See application file for complete search history.

(56) References Cited

U.S. PATENT DOCUMENTS

2007/0146632 A1* 6/2007 Chipman ...................... 351/205
2008/0063998 A1* 3/2008 Liang et al. ..................... 433/29
2009/0247862 A1* 10/2009 Meyer et al. ................. 600/425

FOREIGN PATENT DOCUMENTS

EP 2243420 A1 10/2010
WO 2010122118 A1 10/2010

OTHER PUBLICATIONS

Pircher, et al., "Human Macula Investigated in Vivo with Polarization-Sensitive Optical Coherence Tomography", Investigative Ophthalmology & Visual Science, Dec. 2006; vol. 47, No. 12, pp. 5487-5494.

* cited by examiner

*Primary Examiner* — Weiwen Yang
(74) *Attorney, Agent, or Firm* — Canon USA Inc. IP Division

(57) ABSTRACT

An image processing apparatus includes an extraction unit configured to extract a region where light is depolarized from a polarization-sensitive tomographic image of a subject, and a display control unit configured to display, on a display unit, a region determined as a region invading a predetermined layer of the subject, in a part of the region where light is depolarized.

19 Claims, 10 Drawing Sheets

IMAGE PROCESSING APPARATUS AND IMAGE PROCESSING METHOD

BACKGROUND OF THE INVENTION

1. Field of the Invention

The present invention relates to an image processing apparatus and an image processing method for processing an image of a subject.

2. Description of the Related Art

Optical coherence tomography (hereinafter referred to as OCT) utilizing multiwavelength lightwave interference can acquire a tomographic image of a sample (especially, a fundus) at a high resolution.

In recent years, ophthalmologic OCT apparatuses have acquired a polarization-sensitive OCT image by imaging a fundus tissue with use of a polarization parameter (retardation and orientation), which is one of optical characteristics of the fundus tissue, in addition to acquiring a normal OCT image by imaging a shape of the fundus tissue.

According to polarization-sensitive OCT, the polarization-sensitive OCT image is constructed using the polarization parameter, allowing discrimination and segmentation of the fundus tissue. According to polarization-sensitive OCT, light modulated into circularly-polarized light is used as measurement light for observing a sample, and interference light is divided and detected as two perpendicular linearly-polarized light beams to generate the polarization-sensitive OCT image (refer to WO2010/122118A1). However, WO2010/122118A1 discusses no method for aiding diagnosis, which is an original purpose of polarization-sensitive OCT, more specifically, a method for effectively confirming a lesion generated on a retina layer and the like.

SUMMARY OF THE INVENTION

The present invention is directed to effectively providing a portion that may affect a visual function of a subject's eye in a region extracted from a polarization-sensitive OCT image, to a user.

According to an aspect of the present invention, an image processing apparatus includes a tomographic image acquisition unit configured to acquire a polarization-sensitive tomographic image of a subject, an extraction unit configured to extract a region where light is depolarized from the polarization-sensitive tomographic image, a determination unit configured to determine whether there is a region invading a predetermined layer of the subject, in a part of the region where light is depolarized, and a display control unit configured to display, on a display unit, a region determined by the determination unit as the region of invasion.

According to another aspect of the present invention, an image processing method includes acquiring a polarization-sensitive tomographic image of a subject, extracting a region where light is depolarized from the polarization-sensitive tomographic image, determining whether there is a region invading a predetermined layer of the subject, in a part of the region where light is depolarized, and displaying, on a display unit, a region determined by the determining as the region of invasion.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

A photographing apparatus according to an exemplary embodiment of the present invention can be employed for a subject such as a subject's eye, skin, and an internal organ. Further, the photographing apparatus according to the exemplary embodiment of the present invention is, for example, an ophthalmologic apparatus or an endoscope. In the following description, an ophthalmologic apparatus according to the present exemplary embodiment will be described as an example of the present invention in detail with reference to drawings.

[Overall Configuration of Apparatus]

Figure 1:
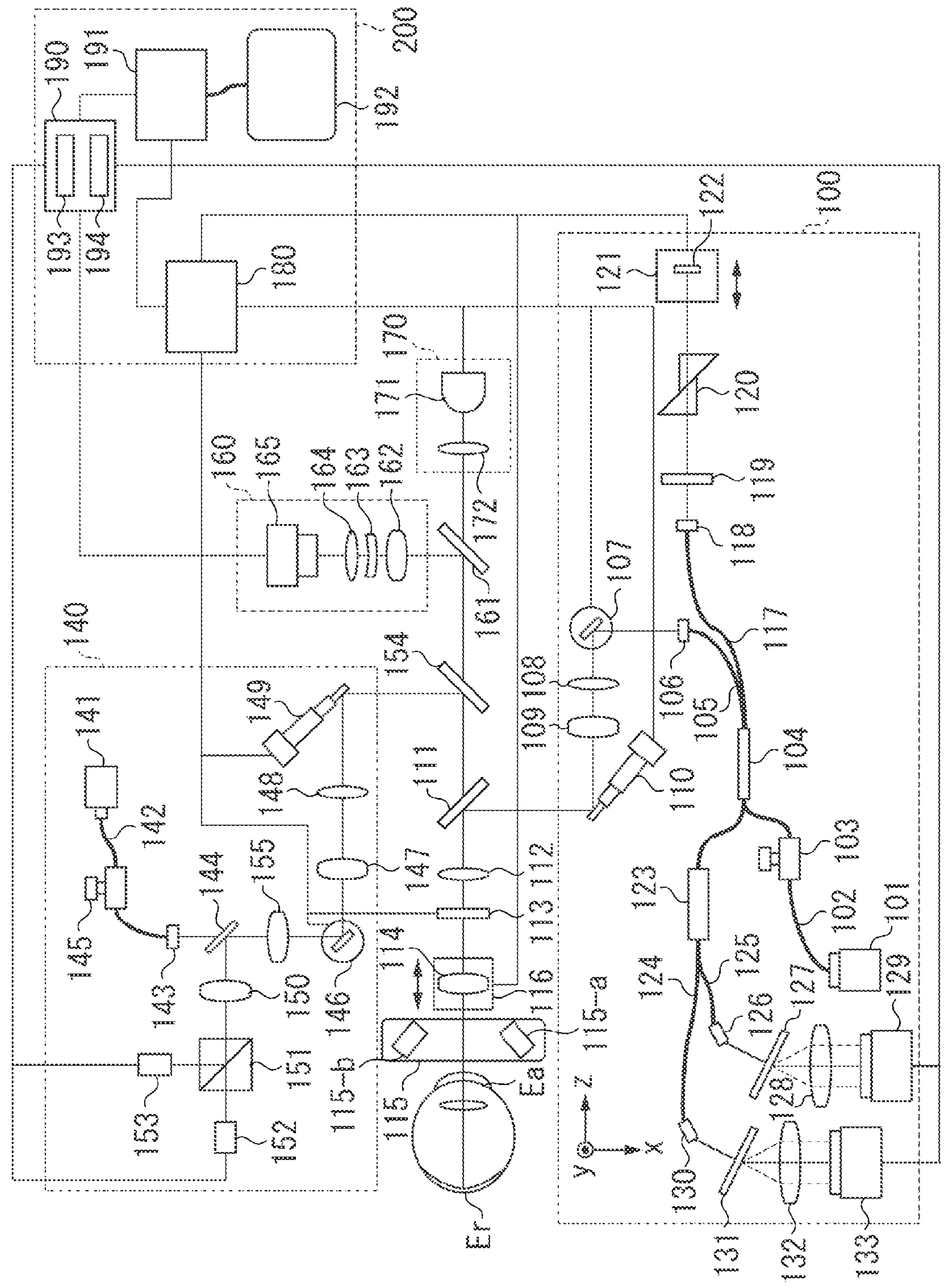
FIG. 1 illustrates an outline of a whole configuration of an image processing apparatus according to an exemplary embodiment of the present invention.

FIG. 1 illustrates an outline of a whole configuration of an ophthalmologic photographing apparatus according to the present exemplary embodiment. At least a part of a signal processing unit 190, which will be described below, can be considered as an "image processing apparatus". In this case, a whole "ophthalmologic apparatus" can be also considered as an "ophthalmologic system", or a whole "photographing apparatus" can be also considered as a "photographing system".

The present apparatus includes a polarization-sensitive OCT (Polarization Sensitive OCT; hereinafter referred to as PS-OCT) 100, a scanning ophthalmoscope using polarization (Polarization Sensitive Scanning Laser Ophthalmoscope; hereinafter referred to as PS-SLO) 140, an anterior eye imaging unit 160, an internal fixation light 170, and a control unit 200.

Alignment of the apparatus is performed with use of an image of an anterior eye of a subject, which is observed by the anterior eye imaging unit 160, in such a state where the internal fixation light 170 is turned on and is focused on the subject's eye. After completion of the alignment, the PS-OCT 100 and the PS-SLO 140 capture an image of a fundus.

<Configuration of PS-OCT 100>

A configuration of the PS-OCT 100 will be described.

A light source 101 is a super luminescent diode (SLD) light source, which is a low coherent light source, and emits, for example, light having a central wavelength of 850 nm and a bandwidth of 50 nm. An SLD is used as the light source 101, but the light source 101 may be realized by any light source capable of emitting low coherent light, such as an amplified spontaneous emission (ASE) light source.

Light emitted from the light source 101 is guided to a fiber coupler 104 having a polarization holding function via a polarization maintaining (PM) fiber 102 and a polarization controller 103, and is divided into measurement light (hereinafter also referred to as "measurement light for tomographic image" or "OCT measurement light") and reference light corresponding to the measurement light.

The polarization controller 103 adjusts a polarized state of the light emitted from the light source 101, and adjusts the light into linearly-polarized light. A division ratio of the fiber coupler 104 is 90 (reference light):10 (measurement light).

The measurement light is emitted from a collimator 106 via a PM fiber 105 as collimated light. The emitted measurement light reaches a dichroic mirror 111 via an X scanner 107 constituted by a galvanometer mirror that horizontally scans a fundus Er with the measurement light, lenses 108 and 19, and a Y scanner 110 constituted by a galvanometer mirror that vertically scans the fundus Er with the measurement light. The X scanner 107 and the Y scanner 110 are controlled by a driving control unit 180 and can scan a predetermined range of the fundus Er with the measurement light. The range on the fundus Er scanned with the measurement light can be considered as a range where a tomographic image is acquired, a position where a tomographic image is acquired, and a position where the measurement light is applied. Further, the X scanner 107 and the Y scanner 110 are an example of a scanning unit for the PS-OCT 100, and may be configured as a common XY scanner. The dichroic mirror 111 has a characteristic of reflecting light of 800 nm to 900 nm and allowing transmission of other light.

The measurement light reflected by the dichroic mirror 111 is controlled to be polarized into circularly-polarized light having a phase shifted 90 degrees by transmission through a λ/4 polarizing plate 113, which is disposed in such a manner that P-polarized light is tilted at 45° relative to S-polarized light about an optical axis as a rotational axis, via the lens 112. The λ/4 polarizing plate 113 is an example of a polarization adjustment member for the measurement light, which adjusts a polarized state of the measurement light. If the PS-SLO optical system 140, which will be described below, is employed, the λ/4 polarizing plate 113 can be disposed on a common optical path shared by a part of the PS-OCT optical system 110 and a part of the PS-SLO optical system 140. As a result, it is possible to comparatively reduce a variation in a polarized state, which is generated between images acquired by the PS-SLO optical system. 140 and the PS-OCT optical system 110. In this case, a scanning unit for the PS-SLO 140 and a scanning unit for the PS-OCT 110 can be disposed at positions conjugate to each other, and can be disposed at positions conjugate to a subject's eye. The inclination of the λ/4 polarizing plate 113 is an example of the state of the λ/4 polarizing plate 113, and is, for example, an angle relative to a predetermined position about an optical axis of a polarization division surface of a fiber coupler 123 with a polarization beam splitter built therein as a rotational axis.

Further, the λ/4 polarizing plate 113 can be configured to be inserted into and removed from an optical path. For example, the λ/4 polarizing plate 113 may be mechanically configured so as to be able to rotate about an optical axis or an axis parallel to the optical axis as a rotational axis. As a result, it is possible to realize a small-sized apparatus capable of easily switching an SLO optical system and the PS-SLO optical system 140. Further, it is possible to realize a small-sized apparatus capable of easily switching an OCT optical system and the PS-OCT optical system 100.

Light incident on the subject's eye is controlled to be polarized into circularly-polarized light by disposing the λ/4 polarizing plate 113 so as to be tilted at 45°, but may not be polarized into circularly-polarized light at the fundus Er depending on the characteristic of the subject's eye. Therefore, the λ/4 polarizing plate 113 is configured in such a manner that the inclination thereof can be finely adjusted under control of the driving control unit 180.

The measurement light controlled to be polarized into circularly-polarized light is focused on a retina layer of the fundus Er by a focus lens 114 placed on a stage 116 via an anterior eye Ea of the eye to be examined. The measurement light applied to the fundus Er is reflected and scattered on each retina layer, and returns back to the fiber coupler 104 along the above-described optical route.

On the other hand, the reference light divided by the fiber coupler 104 is emitted from a collimator 118 via a PM fiber 117 as collimated light. The emitted reference light is controlled to be polarized by a λ/4 polarizing plate 119, which is disposed in such a manner that P-polarized light is tilted at 22.5° relative to S-polarized light about an optical axis as a rotational axis, in a similar manner to the measurement light. The λ/4 polarizing plate 119 is an example of a polarization adjustment member for the reference light, which adjusts a polarized state of the reference light. The reference light is reflected by a mirror 122 on a coherence gate stage 121 via a scattering compensation glass 120, and returns back to the fiber coupler 104. The reference light is returned to the fiber coupler 104 as linearly-polarized light by transmission through the λ/4 polarizing plate 119 twice.

The coherence gate stage 121 is controlled by the driving control unit 180 to deal with, for example, a difference in an axial length of the subject's eye. The coherence gate means a position in the optical path of the measurement light corresponding to an optical path length of the reference light. According to the present exemplary embodiment, the optical path length of the reference light is changed, but the present exemplary embodiment can be configured in any manner as long as the present exemplary embodiment can change an optical path length difference between the optical path of the measurement light and the optical path of the reference light.

Further, the light returned to the fiber coupler 104 and the reference light are combined to form interference light (hereinafter also referred to as "combined light"). The interference light is incident on the fiber coupler 123 incorporating the polarization beam splitter therein, and is divided into P-polarized light and S-polarized light, which are light beams in different polarization directions, at a division ratio of 50:50.

The P-polarized light transmitted through a PM fiber 124 and a collimator 130, is divided by a grating 131, and is received by a lens 132 and a line camera 133. Similarly, the S-polarized light transmitted through a PM fiber 125 and a collimator 126, is divided by a grating 127, and is received by a lens 128 and a line camera 129. The gratings 127 and 131 and the line cameras 129 and 133 are disposed along a direction of each polarized light beam.

The light received by each of the line cameras 129 and 133 is output as an electric signal according to an intensity of the light, and is received by the signal processing unit 190, which is an example of a tomographic image generation unit.

The inclinations of the λ/4 polarizing plates 113 and 119 can be automatically adjusted based on the inclination of the polarization division surface of the polarization beam splitter, but may also be automatically adjusted relative to a line connecting a center of a optic papilla and a center of a macula of the fundus. In this case, the PC-OCT 100 can include an inclination detection unit (not illustrated) configured to detect the inclinations of the λ/4 polarizing plates 113 and 119. It is possible to detect a current inclination and achievement of a predetermined inclination by this inclination detection unit. Alternatively, how much the λ/4 polarizing plates 113 and 119 are tilted may be detected based on an intensity of received light, and the inclinations may be adjusted so as to achieve a predetermined intensity. As will be described below, the present exemplary embodiment may be configured so as to display an object that indicates the inclination on a graphical user interface (GUI) to allow a user to adjust the inclination with use of a mouse. Further, a similar effect can be also acquired by adjusting the polarization beam splitter and the λ/4 polarizing plates 113 and 119 based on a vertical direction as a polarization reference.

<Configuration of PS-SLO 140>

A configuration of the PS-SLO 140 will be described.

A light source 141 is a semiconductor laser. According to the present exemplary embodiment, the light source 141 emits, for example, light having a central wavelength of 780 nm. Measurement light emitted from the light source 141 (hereinafter also referred to as "measurement light for a fundus image" or "SLO measurement light") is controlled to be polarized into linearly-polarized light by a polarization controller 145 via a PM fiber 142, and is output from a collimator 143 as collimated light. The output measurement light is transmitted via a perforated portion of a perforated mirror 144 and a lens 155, and reaches a dichroic mirror 154 via an X scanner 146 constituted by a galvanometer mirror that horizontally scans the fundus Er with the measurement light, lenses 147 and 148, and a Y scanner 149 constituted by a galvanometer mirror that vertically scans the fundus Er with the measurement light. The X scanner 146 and the Y scanner 149 are controlled by the driving control unit 180, and can scan a desired range on the fundus Er with the measurement light. The X scanner 146 and the Y scanner 149 are an example of a scanning unit for the PS-SLO 140, and may be also configured as a common XY scanner. The dichroic mirror 154 has a characteristic of reflecting light of 760 nm to 800 nm and allowing transmission of other light.

The measurement light as linearly-polarized light reflected by a dichroic mirror 154 reaches the fundus Er via an optical path similar to the PS-OCT 100.

The measurement light applied to the fundus Er is reflected and scattered by the fundus Er, and reaches the perforated mirror 144 via the above-described optical path. The light reflected by the perforated mirror 144 is transmitted through the lens 150, is divided by a polarization beam splitter 151 into light beams polarized in different directions (in the present exemplary embodiment, P-polarized light and S-polarized light). The divided light is received by avalanche photo diodes (APDs) 152 and 153, is converted into an electric signal, and is received by the signal processing unit 190, which is an example of the fundus image generation unit.

The perforated mirror 144 is positioned so as to be conjugate to a pupil position of the subject's eye. After the measurement light applied to the fundus Er is reflected and scattered, a part of this light which is transmitted through a vicinity of the pupil is reflected by the perforated mirror 144.

The present exemplary embodiment uses the PM fiber for both the PS-OCT 100 and PS-SLO 140, but a similar configuration and effect is realized by controlling polarization with use of a polarization controller, even when the PM fiber is replaced with a single mode fiber (SMF).

<Anterior Eye Imaging Unit 160>

The anterior eye imaging unit 160 will be described.

The anterior eye imaging unit 160 illuminates the anterior eye Ea by a illumination light source 115, which is constituted by light emitting diodes (LEDs) 115-*a* and 115-*b* configured to emit illumination light having a wavelength of 1000 nm. Light reflected by the anterior eye Ea reaches a dichroic mirror 161 via a lens 114, the λ/4 polarizing plate 113, the lens 112, and the dichroic mirrors 111 and 154. The dichroic mirror 161 reflects light of 980 nm to 1100 nm and transmits other light, as its characteristic. The light reflected by the dichroic mirror 161 is received by an anterior eye camera 165 via lenses 162, 163, and 164. The light received by the anterior eye camera 165 is converted into an electric signal, and is received by the signal processing unit 190.

<Internal Fixation Light 170>

The internal fixation light 170 will be described.

The internal fixation light 170 includes an internal fixation light display unit 171 and a lens 172. A plurality of light-emitting diodes (LDs) arranged in a matrix is used as the internal fixation light display unit 171. The light emission positions of the light-emitting diodes are changed under control of the driving control unit 180 according to a portion to be imaged. Light from the internal fixation light display unit 171 is guided into the subject's eye via a lens 172. The internal fixation light display unit 171 emits light of 520 nm, and a desired pattern is displayed by the control unit 180.

<Control Unit 200>

The control unit 200 for controlling the whole apparatus will be described. The control unit 200 includes the driving control unit 180, the signal processing unit 190, a display control unit 191, and a display unit 192.

The driving control unit 180 controls each unit in the above-described manner.

The signal processing unit 190 includes an image generation unit 193 and an image analysis unit 194. The signal processing unit 190 generates an image, analyzes the generated image, and generates visualized information of an analysis result based on signals respectively output from the line cameras 129 and 133, the APDs 152 and 153, and the anterior eye camera 165. The generation and analysis of an image will be described in detail below.

Images generated by a fundus image generation unit and a tomographic image generation unit are acquired by a fundus image acquisition unit (not illustrated) and a tomographic image acquisition unit (not illustrated), and the display control unit 191 displays the acquired images and the like on a display screen of the display unit 192. The display unit 192 is, for example, a liquid crystal display. Image data generated by the signal processing unit 190 may be transmitted to the display control unit 191 by wired communication or wireless communication. In this case, the display control unit 191 can be considered as the image processing apparatus. As a photographing system, the present exemplary embodiment may be configured such that the fundus image acquisition unit includes the SLO optical system and the tomographic image acquisition unit includes the OCT optical system. In the present specification, in a case of subjects other than an eye, the term "fundus image (fundus luminance image)" can be replaced with the term "planar image (planar luminance image)", and the term "fundus image acquisition unit" can be replaced with the term "planar image acquisition unit".

The display unit 192 displays a display form that indicates various kinds of information under control of the display control unit 191, as will be described below. Image data from the display control unit 191 may be transmitted to the display unit 192 by wired communication, or wireless communication. Further, the display unit 192 is included in the control unit 200. However, the present invention is not limited thereto, and the display unit 192 may be provided as a separate component from the control unit 200. Further, the display control unit 191 and the display unit 192 may be an integrally configured tablet that is an example device portable by a user. In this case, a touch panel function can be provided in the display unit 192, and the display unit 192 can be desirably configured so as to allow a user to operate the display, for example, move a displayed position in an image, enlarge and reduce an image, and change a displayed image on the touch panel.

[Image Processing]

Next, image generation by the image generation unit 193, which is included in the signal processing unit 190, will be described.

The image generation unit 193 performs reconstruction processing which is used in standard spectral domain OCT (SD-OCT), on respective interference signals output from the line cameras 129 and 133, thereby generating a tomographic image corresponding to first polarized light and a tomographic image corresponding to second polarized light, which are two tomographic images based on the respective polarization components.

First, the image generation unit 193 removes a fixed pattern noise from the interference signal. The image generation unit 193 removes the fixed pattern noise by averaging a plurality of detected A-scan signals to extract the fixed pattern noise, and subtracting this noise from the input interference signal.

Next, the image generation unit 193 converts the interference signal from a wavelength into a wave number, and performs Fourier transform, thereby generating a tomographic signal that indicates a polarized state.

Two tomographic images are generated by performing the above-described processing on the interference signals of the two polarization components.

Further, the image generation unit 193 aligns signals output from the APDs 152 and 153 in synchronization with driving of the X scanner 146 and Y scanner 149, thereby generating a fundus image corresponding to the first polarized light and a fundus image corresponding to the second polarized light, which are two fundus images based on the respective polarization components.

<Generation of Tomographic Luminance Image or Fundus Luminance Image>

The image generation unit 193 generates a tomographic luminance image from the above-described two tomographic signals.

The tomographic luminance image is basically similar to a tomographic image acquired by a conventional OCT. A pixel value r of the tomographic luminance image is calculated from tomographic signals $A_H$ and $A_V$ acquired from the respective line cameras 129 and 133 according to an EXPRESSION 1.

$$r=\sqrt{A_H^2+A_V^2} \quad \text{(EXPRESSION 1)}$$

Further, similarly, a fundus luminance image is generated from the two fundus images.

Figure 2A:
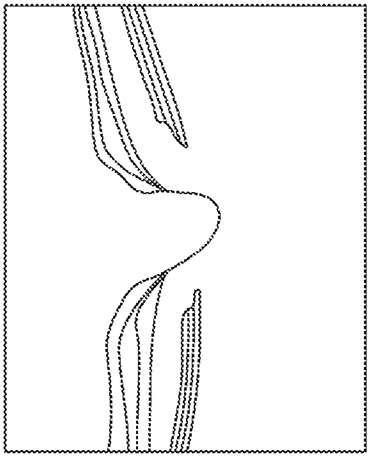
FIGS. 2A to 2E illustrate examples of images captured by the image processing apparatus according to the exemplary embodiment of the present invention.

FIG. 2A illustrates an example of a luminance image of an optic papilla portion.

When the λ/4 polarizing plate 113 is retracted from the optical path, the display control unit 191 may display a tomographic luminance image acquired by a conventional OCT method on the display unit 192, and may display a fundus luminance image acquired by a conventional SLO method on the display unit 192.

<Generation of Retardation Image>

The image generation unit 193 generates a retardation image from tomographic images of polarization components perpendicular to each other.

A value δ of each pixel in a retardation image is a value indicating a ratio of influences that a vertical polarization component and a horizontal polarization component receive from the subject's eye at a position of each of pixels constituting a tomographic image, and is calculated from the respective tomographic images $A_H$ and $A_V$ according to an EXPRESSION 2.

$$\delta=\arctan\left[\frac{A_V}{A_H}\right] \quad \text{(EXPRESSION 2)}$$

Figure 2B:
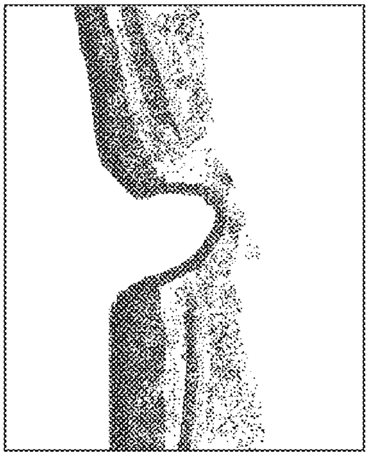

FIG. 2B illustrates an example of a thus-generated retardation image of the optic papilla portion. This image can be acquired by calculation of the EXPRESSION 2 as to each B-scan image. As described above, the retardation image is a tomographic image that indicates a difference between the influences that the two polarized light beams receive from the subject's eye. FIG. 2B displays a value indicating the above-described ratio in full color as a tomographic image. A dark portion in the image suggests that the value indicating the above-described ratio is small, and a light portion in the image suggests that the value indicating the above-described ratio is large. Therefore, it is possible to recognize a birefringent layer by generating the retardation image. The details thereof are described in "Opt. Express 13, 10217, 2005 written by E. Gotzinger et al".

Further, similarly, the signal processing unit 190 can also generate a retardation image in a planar direction of the fundus based on outputs from the APDs 152 and 153.

<Generation of Retardation Map>

The image generation unit 193 generates a retardation map based on retardation images acquired from a plurality of B-scan images.

First, the image generation unit 193 detects a retinal pigment epithelium (hereinafter referred to as "RPE") in each B-scan image. Because the RPE has a depolarizing property, the image generation unit 193 examines distribution of retardation from an inner limiting membrane (hereinafter also referred to as "ILM") within a range that does not include the RPE, along a depth direction of each A-scan, and sets a maximum value thereof as a representative value of retardation in this A-scan.

The image generation unit 103 generates the retardation map by performing the above-described processing on all retardation images.

Figure 2C:
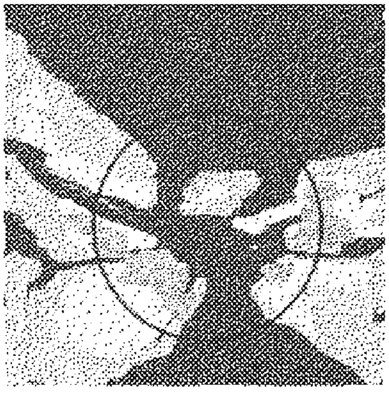

FIG. 2C illustrates an example of a retardation map of the optic papilla portion. A dark portion in the image suggests that a value indicating the above-described ratio is small, and a light portion in the image suggests that a value indicating the above-described ratio is large. In the optic papilla portion, a birefringent layer is a retinal nerve fiber layer (hereinafter also referred to as "RNFL"), and the retardation map is an image that indicates a difference between influences that the two polarized light beams receive from a birefringence and thickness of the RNFL. Therefore, a value indicating the above-described ratio is large in a portion where the RNFL is thick, while a value indicating the above-described ratio is small in a portion where the RNFL is thin. Therefore, the retardation map allows a user to grasp the thickness of the RNFL in the whole fundus, and therefore can be used for diagnosis of glaucoma.

<Generation of Birefringence Map>

The image generation unit 193 linearly approximates values of retardation δ within the range from the ILM to the RNFL in each A-scan image of the previously generated retardation image, and sets an inclination thereof as a birefringence at a position of the retina with respect to this A-scan image. In other words, the retardation is a product of a distance and a birefringence in the RNFL, whereby it is possible to acquire a linear relationship by plotting values of depth and retardation in each A-scan image. Therefore, this plot is linearly approximated by the least square method and the like to acquire an inclination thereof. The acquired inclination is set as a value of birefringence of the RNFL in this A-scan image. The image forming unit 193 generates a map indicating the birefringence by performing this processing on all of acquired retardation images.

Figure 2D:
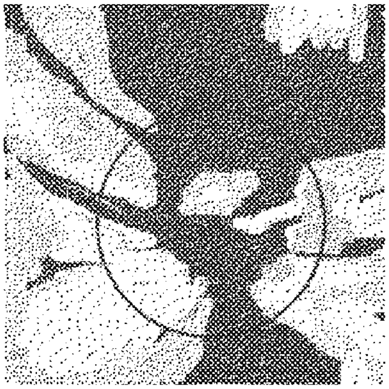

FIG. 2D illustrates an example of a birefringence map of the optic papilla portion. The birefringence map is generated by directly mapping birefringence values. Therefore, even when a fiber structure of the RNFL changes while a thickness of the RNFL does not change, this change can be visualized as a birefringence change.

<Generation of DOPU Image>

The image generation unit 193 calculates a Stokes vector S for each pixel from the acquired tomographic signals $A_H$ and $A_V$ and a phrase difference Δφ therebetween according to an EXPRESSION 3.

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \quad \text{(EXPRESSION 3)}$$

In this expression, Δφ is calculated from phases $\phi_H$ and $\phi_V$ of the respective signals acquired when the two tomographic images are calculated, by $\Delta\phi=\phi_V-\phi_H$.

Next, the image generation unit 193 sets, in each B-scan image, a window having a size of approximately 70 μm and approximately 18 μm in substantially a main scanning direction and a depth direction of the measurement light. Then, in each window, the image generation unit 193 averages respective elements in the Stokes vectors, each of which is calculated for each pixel according to the EXPRESSION 3. Then, the image generation unit 193 calculates a degree of polarization uniformity (DOPU) in this window according to an EXPRESSION 4.

$$\text{DOPU}=\sqrt{Q_m^2+U_m^2+V_m^2} \quad \text{(EXPRESSION 4)}$$

Figure 2E:
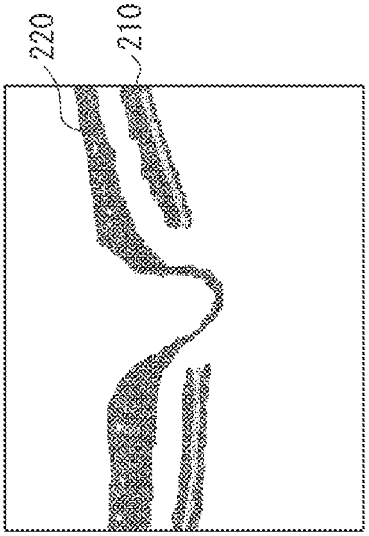

In this expression, $Q_m$, $U_m$, and $V_m$ represent values acquired by averaging elements Q, U, and V in the Stokes vectors in each window. The DOPU image of the optic papilla portion illustrated in FIG. 2E is generated by performing this processing on all windows in the B-scan image. As described above, the DOPU image is a tomographic image that indicates uniformity in two types of polarization.

The DOPU is a numerical value that indicates uniformity of polarization, and has a numerical value close to 1 as to a portion where polarization is maintained while having a numerical value smaller than 1 as to a portion where light is depolarized and polarization is not maintained. According to a structure in the retina, RPE has a property of depolarizing a polarized state, whereby the value of DOPU is smaller in a portion corresponding to the RPE than the other regions in the DOPU image. In FIG. 2E, a light portion 210 in the image indicates the REP, and a dark portion 220 in the image indicates a retina layer region where polarization is maintained. The DOPU image visualizes a depolarizing layer such as the RPE, whereby it is possible to more reliably visualize the RPE than a change in a luminance visualizes, even when the PRE is deformed due to, for example, disease.

Further, similarly, the signal processing unit 190 can generate a DOPU image in a planar direction of the fundus base on outputs from the APDs 152 and 153.

In the present specification, the above-described tomographic images corresponding to the first and second polarized light beams, retardation image, and DOPU image are also referred to as a tomographic image or a polarization-sensitive tomographic image that indicates a polarization state. Further, in the present specification, the above-described retardation map, and birefringence map are also referred to as a fundus image or a polarization fundus image that indicates a polarization state.

[Processing Operation]

Next, a processing operation by the present image processing apparatus will be described.

Figure 3:
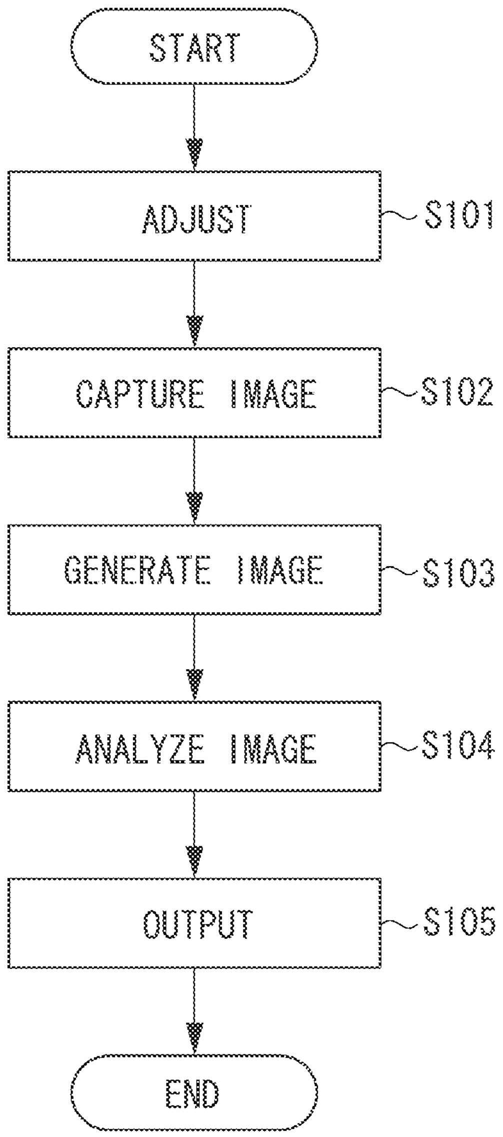
FIG. 3 is a processing flow of the image processing apparatus according to the exemplary embodiment of the present invention.

FIG. 3 is a flowchart illustrating the processing operation of the present image processing apparatus.

<Adjustment>

First, in step S101, the present apparatus and the subject's eye are aligned with each other in a state where the subject's eye is placed on the present apparatus. Regarding the alignment, processing peculiar to the present exemplary embodiment will be described, but alignment of a working distance and the like in XYZ directions, focusing, adjustment of the coherence gate, and the like will be not described specifically, since they are commonly practiced techniques.

(Adjustment of Imaging Position of PS-OCT)

Figure 4:
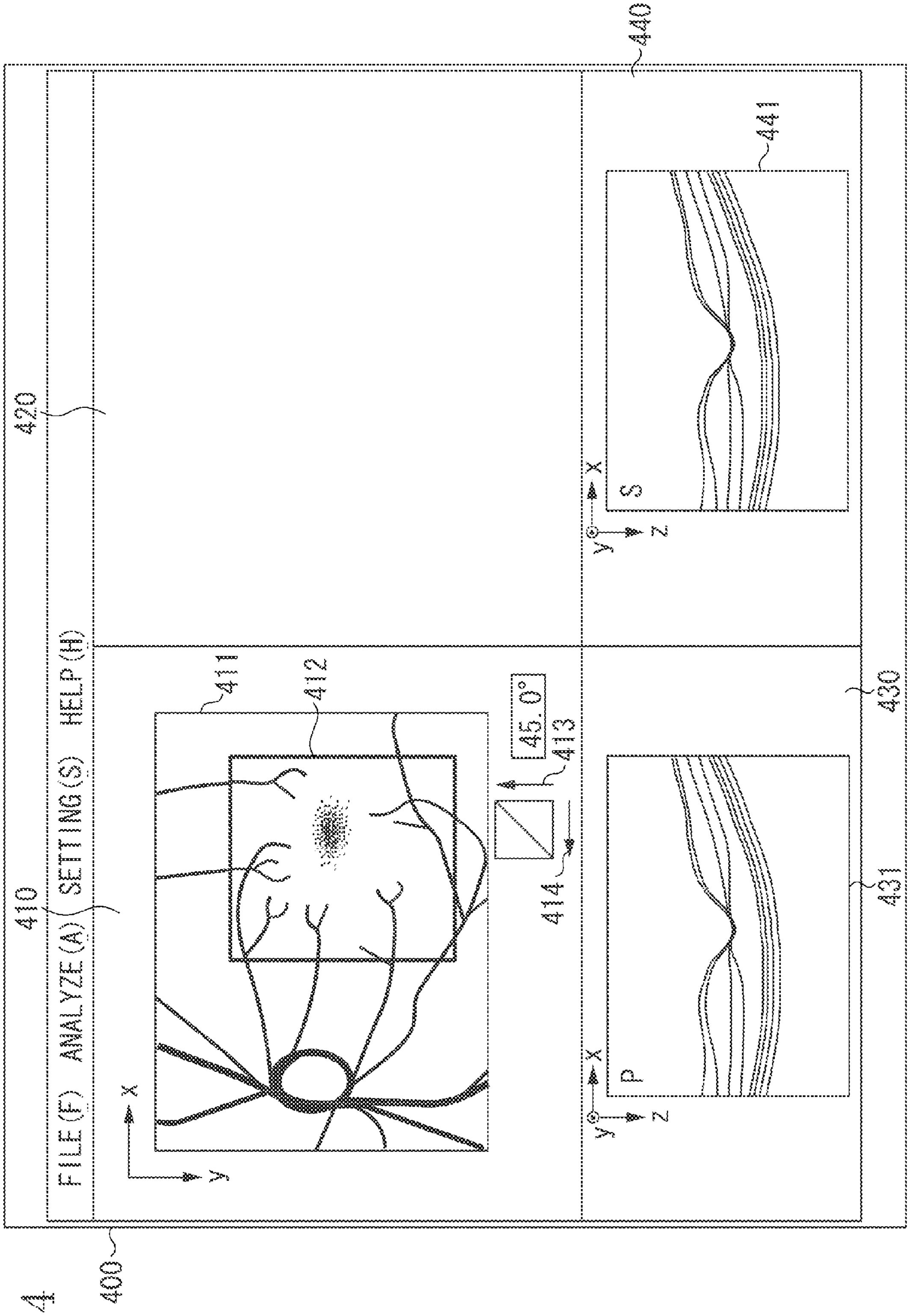
FIG. 4 illustrates an example of a screen for photographing a tomographic image.

FIG. 4 illustrates a window 400 displayed on the display unit 192 at the time of adjustment. A fundus image 411, which is captured by the PS-SLO 140 and generated by the signal processing unit 190, is displayed in a display area 410, which is an example of a first display area. A frame 412, which indicates an imaging range of the PS-OCT 100, is displayed being superimposed on the fundus image 411.

A user sets an imaging range under control of the driving control unit 180 by issuing an instruction through specifying the range with a cursor displayed on the window 400, and performing a click operation, a drag operation, and the like with use of an instruction device (not illustrated) such as a mouse. In other words, the user can move the frame 412 by specifying the frame 412 with the cursor and performing a drag operation. In response thereto, the driving control unit 180 sets the imaging range by controlling a driving angle of the scanner. The mouse in the present exemplary embodiment includes, for example, a sensor configured to detect a movement signal when the mouse body is two-dimensionally moved by a user's hand, two left and right mouse buttons for detecting that the mouse is pressed by the user's hand, and a wheel mechanism provided between the two left and right mouse buttons rotatably in front-back and left-right direction. Further, the instruction device may be realized by providing a touch panel function in the display unit 192 to allow the user to specify an acquisition position on the touch panel.

(Adjustment of λ/4 Polarizing Plate)

An adjustment of the λ/4 polarizing plate 113 will be described.

Referring to FIG. 4, instruction portions 413 and 414 are displays for adjusting the angle of the λ/4 polarizing plate 113. The user issues an instruction with use of the instruction device to adjust the angle of the λ/4 polarizing plate 113 under control of the driving control unit 180. The instruction portion 413 is a display for issuing an instruction to make an adjustment in the counterclockwise direction, and the instruction portion 414 is a display for issuing an instruction to make an adjustment in the clockwise direction. A numeral value displayed next to the instruction portions 413 and 414 indicates the current angle of the λ/4 polarizing plate 113. The display control unit 191 may display an instruction portion for adjusting the angle of the λ/4 polarizing plate 119 on the display unit 192 together with the instruction portion 413 side by side, or may display the instruction portion for adjusting the angle in place of the instruction portion 413.

The user issues an instruction with the cursor with use of the mouse so that tomographic images of the polarized light beams respectively displayed on a display area 430, which is an example of a third display area, and a display area 440, which is an example of a fourth display area, have a same luminance. The present exemplary embodiment may be configured such that peak luminance values are displayed together with the tomographic images 431 and 441 of the respective polarized light beams, or waveforms of the respective interference signals themselves are displayed, allowing the user to make an adjustment while viewing them. The tomographic images 431 and 441 of the respective polarized light beams are examples of tomographic images corresponding to the first polarized light and the second polarized light, respectively. A indication of types of the respective images, such as the character "P" indicating P-polarized light and the character "S" indicating S-polarized light, is desirably displayed being superimposed on the tomographic images 431 and 441 (or tomographic images 531 and 541, which will be described below) of the respective polarized light beams. Providing these displays can prevent the user from erroneously recognizing the images. The indication can also be displayed above or adjacent to the images, instead of being displayed while being superimposed on the images. The indication may be displayed in any manner as long as they are displayed so as to correspond to the images.

Further, nothing may be displayed on a display area 420, which is an example of a second display area, at this stage. Alternatively, during automatic adjustment and the like, an indication of a current adjustment state, such as a message "λ/4 POLARIZING PLATE IS BEING ADJUSTED NOW" may be displayed on the display area 420. Further, an indication of patient information such as whether the subject' eye is a left eye or a right eye, and an indication of photographing information such as a photographing mode may be displayed on the window 400. It is desirable to repeat insertion and removal of the λ/4 polarizing plate 113 relative to the optical path to alternately acquire the fundus luminance image and the tomographic image that indicate a polarized state. Thus, for example, the display control unit 191 can display the fundus luminance image on the display area 410, and the tomographic image that indicates a polarized state on the display area 420, while the size of the ophthalmologic apparatus can be reduced as much as possible.

Desirably, an alignment adjustment using an image of an anterior eye and a luminescent spot in a cornea, a focus adjustment using a fundus image indicating a polarized state, and a coherence gate adjustment using a tomographic image indicating a polarized state, and an adjustment of the λ/4 polarizing plates 113 and 119 can be performed in this order. It is desirable to determine a position where a tomographic image indicating a polarized state is acquired before the coherence gate adjustment using a tomographic image indicating a polarized state. However, this position may be determined in initial setting so as to acquire a central region of a fundus image indicating a polarized state. This allows an easy adjustment so as to correctly acquire a tomographic image indicating a polarized state, which covers more detailed and a narrower range than a fundus image indicating a polarized state. At this time, the λ/4 polarizing plates 113 and 119 may be automatically adjusted upon completion of the coherence gate adjustment, or the λ/4 polarizing plates 113 and 119 may be automatically adjusted in response to an input of a signal for acquiring an image indicating a polarized state. Alternatively, the present exemplary embodiment may be configured such that the λ/4 polarizing plates 113 and 119 are adjusted in advance on an initial setting screen or the like when the ophthalmologic apparatus is started up so that the λ/4 polarizing plates 113 and 119 do not need to be adjusted for each photographing operation.

Further, if the present exemplary embodiment is configured so as to allow insertion and removal of the λ/4 polarizing plates 113 and 119 into and from the optical paths, the adjustments can be performed in the order of the alignment adjustment using an image of an anterior eye and a luminescent spot in a cornea, a focus adjustment using an SLO fundus image, a coherence gate adjustment using an OCT tomographic image, insertion of the λ/4 polarizing plates 113 and 119 into the optical paths, and an adjustment of the λ/4 polarizing plates 113 and 119. This order allows the user to make the adjustments before acquiring an image indicating a polarized state with use of a normal SLO fundus image and OCT tomographic image which the user is intuitively familiar with. However, the coherence gate adjustment using a tomographic image indicating a polarized state of the PS-OCT 100 may also be made after the focus adjustment is made and then the λ/4 polarizing plates 113 and 119 are inserted. In this case, the λ/4 polarizing plates 113 and 119 may be automatically inserted into the optical paths upon completion of the coherence gate adjustment or completion of the focus adjustment. Alternatively, the λ/4 polarizing plates 113 and 119 may be automatically inserted into the optical paths in response to an input of a signal for acquiring an image indicating a polarized state.

As the focus adjustment, a fine focus adjustment using an OCT tomographic image may be made after a rough adjustment using an SLO fundus image.

All of these adjustments may be automatically made in the above-described order, or these adjustments may be made according to, for example, a drag operation with the cursor placed on a slider corresponding to each adjustment, which is displayed on the display unit 192. Further, when the λ/4 polarizing plates 113 and 119 are inserted and removed, an icon for allowing the user to request insertion and removal of the λ/4 polarizing plates 113 and 119 into or from the optical paths may be displayed on the display unit 192.

<Image Capturing>-<Image Generation>

Figure 5:
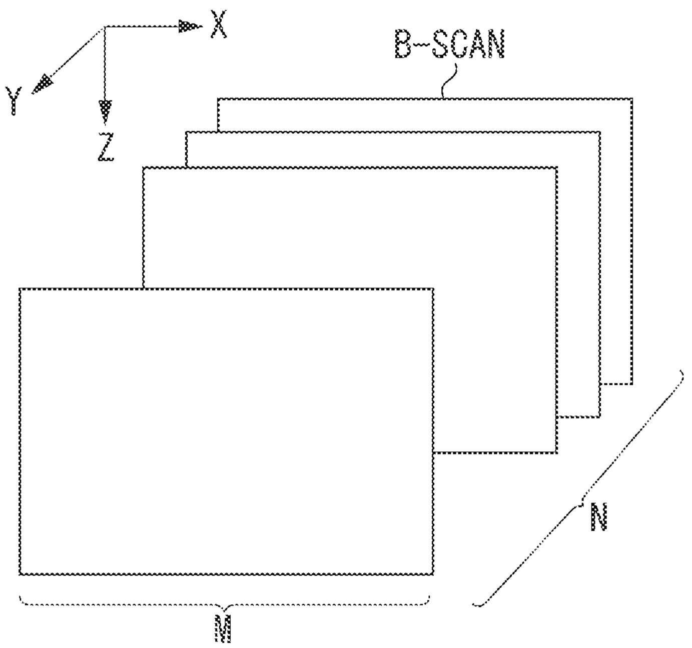
FIG. 5 illustrates a structure of the captured tomographic image.

In steps S102 and S103, the measurement light is emitted from the respective light sources 101 and 141. Light returning from the fundus Er is received by the line cameras 129 and 133, and the APDs 152 and 153, and then the image generation unit 193 generates each image as described above. According to the present exemplary embodiment, as illustrated in FIG. 5, N B-scan images, each of which is constituted by M A-scans, are generated by controlling the X scanner 110 and the Y scanner 107. The numbers M and N can be set based on a time required for photographing and a size of a region required in diagnosis. For example, a region of approximately 8 mm×6 mm around a macula can be covered by setting M and N to values of approximately 1024 and 250, respectively.

<Analysis>

In a tomographic image of a sick eye, a luminance value of the tomographic image may reduce due to an influence of the disease compared to a tomographic image of a healthy eye, and this reduction may lead to an oversight or false detection of retina layers. Therefore, in step S104, the image analysis unit 194 detects each layer of the retina with use of information about a portion where light is depolarized, which is calculated by the image generation unit 193 in step S103.

It is possible to detect a position of the RPE 210 by calculating the DOPU according to the EXPRESSION 4, since the RPE depolarizes light among the retina layers. Further, it is possible to detect even the whole retina layer 220 that does not depolarize light. As a result, it is possible to detect a luminance value of the RPE in each tomographic image by referring to a luminance value of a portion corresponding to the RPE in a luminance image. Therefore, even in a tomographic image having a low luminance value as a whole due to an influence of a disease, a region of the whole retina layer, a position of the RPE, and a luminance value corresponding to the RPE can be detected, so that it is possible to reduce an oversight and false detection due to the disease.

An example of a method for detecting a boundary of each layer of the retina is to use a luminance value acquired from a position calculated by the DOPU calculation according to the EXPRESSION 4 as a threshold value in layer detection. For example, a threshold value used in detection of a boundary of each layer of a healthy eye is set in advance. Then, average luminance values of the RPE and the whole retina layer region are also set in advance. A luminance value of the RPE and a luminance value of the whole retina layer region acquired from a position obtained from the calculation of the EXPRESSION 4 are compared to the average luminance values set in advance. The threshold value used in detection of a boundary of each layer, which is set in advance, is adjusted according to percentage of a difference between the luminance values. For example, if luminance values of luminance images corresponding to the RPE 210 and the retina layer region 220 in FIG. 2E are lower than the average luminance values set in advance by 10%, the threshold value is reduced by 10% accordingly. Then, the image analysis unit 194 applies a median filter as a kind of smoothing, and a Sobel filter as a kind of edge detection on a tomographic image that is a processing target, respectively, to generate respective images (hereinafter also referred to as "median image" and "Sobel image"). Next, the image analysis unit 194 generates a profile for each A-scan from the generated median image and Sobel image. A profile of luminance values is acquired from the median image, and a profile of inclinations is acquired from the Sobel image. Then, the image analysis unit 194 detects a peak in the profile generated from the Sobel image. The image analysis unit 194 refers to the profile of the median image corresponding to a point in front of or at the back of the detected peak and a point between peaks, and compares it with the previously acquired threshold value to thereby extract each region in the retina layer or the boundary therebetween.

Figure 6:
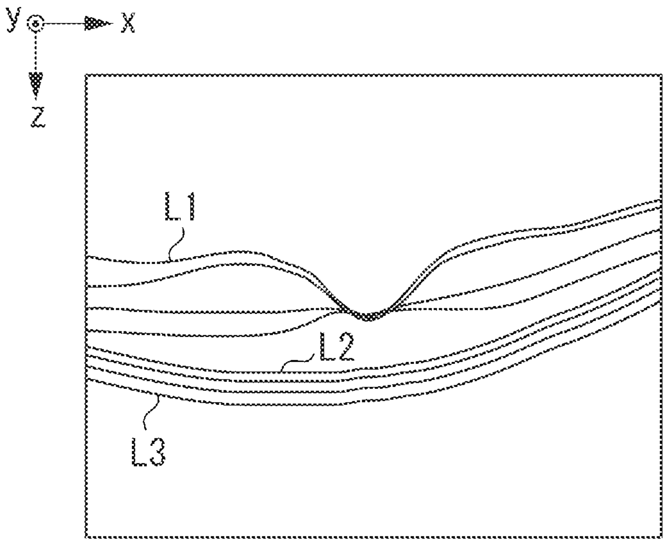
FIG. 6 illustrates a result of layer extraction.

More specifically, according to the present exemplary embodiment, the image analysis unit 194 extracts two layers L1 (inner limiting membrane) and L2 (photoreceptor inner/outer segment junction; hereinafter referred to as IS/OS) as illustrated in FIG. 6. Further, a layer L3 corresponds to the RPE extracted from the DOPU image. Next, the image analysis unit 194 analyzes a positional relationship between the RPE extracted from the DOPU image and the IS/OS.

Figure 7:
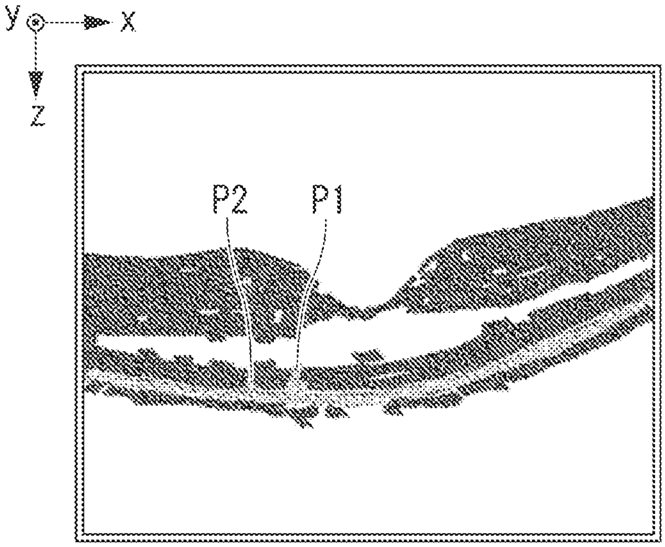
FIG. 7 illustrates a DOPU image having a disease.
Figure 8:
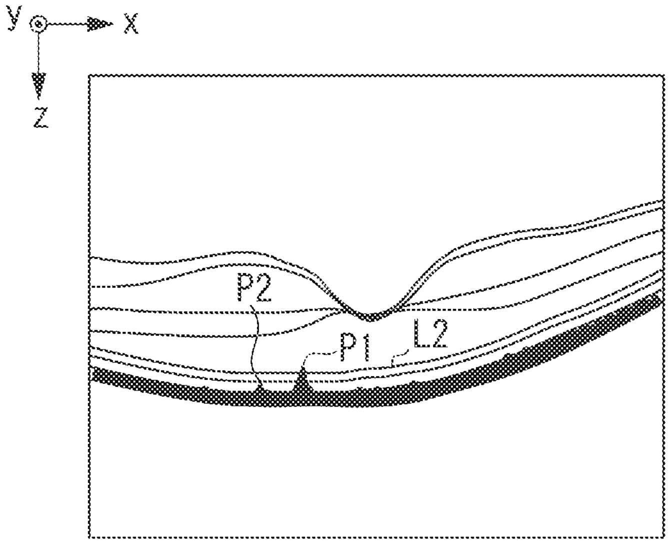
FIG. 8 illustrates a region where light is depolarized and the result of layer extraction in a superimposed state.

FIG. 7 illustrates an example of the DOPU image. There are lesions P1 and P2 at the portion of the RPE. These lesions are objects (substances) having a depolarizing property in a similar manner to the RPE, whereby regions where light is depolarized are visualized in the DOPU image. The region where light is depolarized means, for example, a region where a difference is comparatively large between the influences that the two polarized light receive from the subject's eye. FIG. 7 shows that the regions P1 and P2 different from a normal region of the RPE in the region where light is depolarized are invasive toward the retina inner layer (the regions P1 and P2 protrude from the RPE, or protrusions are formed at a part of the PRE). FIG. 8 is an example of an image generated by superimposing the region where light is depolarized, which is extracted from the DOPU image, on an image resulting from layer extraction. In FIG. 8, the IS/OS is labeled as L2. As seen from FIG. 8, the region P1 (a first region), which is different from the normal PRE in the region where light is depolarized, reaches the IS/OS. On the other hand, the region P2 (a second region), which is different from the normal PRE in the region where light is depolarized, remains below the IS/OS. The IS/OS is a junction of a photoreceptor cell, and existence of a lesion on the IS/OS may lead to visual disability.

Therefore, the image analysis unit 194, which is an example of an extraction unit, extracts a region where light is depolarized from the DOPU image. Next, the image analysis unit 194 extracts a portion that reaches the IS/OS in the region where light is depolarized from each of the B-scan images (tomographic luminance images) illustrated in FIG. 5. As a result, it is possible to locate a portion invading the IS/OS in the region where light is depolarized in the photographed region of the fundus. Further, the image analysis unit 194 generates a map that indicates the position of the invasion extracted from each of the B-scan images.

Figure 9:
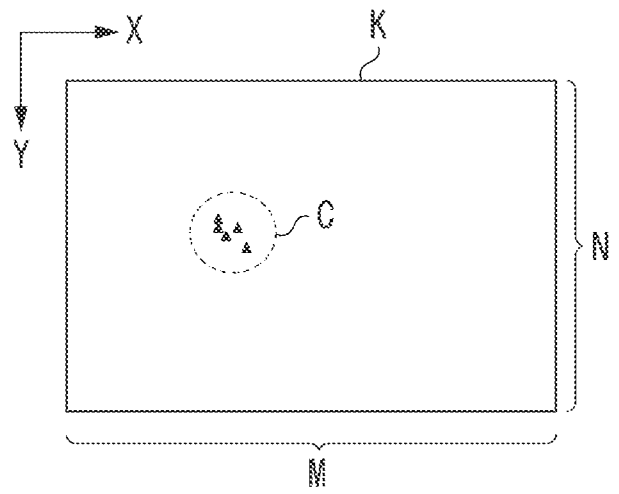
FIG. 9 illustrates an invading portion in the region where light is depolarized.

FIG. 9 is an example thereof, and illustrates a portion C where the invasion reaches the IS/OS in the region where light is depolarized on a map K having a size of M×N. This map K allows efficient confirmation of a portion where the IS/OS may be damaged. The map K may be generated by simply plotting the portion where the invasion reaches the IS/OS in the region where light is depolarized, as illustrated in FIG. 9. Alternatively, the map K may be generated by extracting an edge close to the inner layer in the region where light is depolarized, and visualizing a distance between this edge and the IS/OS. This display allows the user to visually recognize a portion where visual disability may occur although the invasion has not reached the IS/OS yet, like the portion P2 illustrated in FIG. 8.

The image analysis unit 194, which is an example of a determination unit, can desirably determine that, in the region where light is depolarized, a portion located at a position corresponding to a threshold value or a larger value from a predetermined layer (for example, a layer having a visual function) in a depth direction is the invading portion C. As a result, it is possible to automatically extract the invading portion C. When the RPE layer is referred to as a predetermined region, the predetermined layer is referred to as a region other than the predetermined region.

Stargardt's disease may cause such a symptom that the RPE layer protrudes to invade the region having the visual function (IS/OS). However, a normal OCT (a luminance tomographic image) may be unable to clearly reveal whether the RPE layer is invasive.

Therefore, the invading portion is automatically extracted with use of a polarization-sensitive tomographic image to present, for example, the portion invading the region having the visual function, to the user.

More specifically, a portion of a threshold value or a larger value in the depth direction in the RPE layer in the polarization-sensitive tomographic image is automatically extracted as the portion invading the region having the visual function.

The invading portion C may be manually selected by the user with use of a not-illustrated operation unit such as a touch panel and a mouse. Further, after the user manually selects a part of the region where light is depolarized, the invading portion C may be automatically extracted from the selected region.

The present exemplary embodiment has been described based on the method according to which the image analysis unit 194 as an example of the determination unit determines whether a size of the protrusion in the depth direction is a threshold value or larger to determine whether the invasion reaches the IS/OS. However, instead of this method, the present exemplary embodiment may use a method for comparing data with previous normal data when the eye was a healthy eye. In this case, the normal data may be any information that indicates a positional relationship between the RPE and the IS/OS such as a distance from the RPE to the IS/OS and a relative coordinate of the IS/OS to the RPE in a previous polarization-sensitive tomographic image. Alternatively, the present exemplary embodiment may use a method for comparing data with normal data of information that indicates a positional relationship between the RPE and the IS/OS in Normative Data Base (NDB). Further, the present exemplary embodiment may use a method for automatically determining a threshold value of a dimension of the protrusion in the depth direction. For example, this method may be performed by segmenting the IS/OS and the RPE in a tomographic luminance image corresponding to a polarization-sensitive tomographic image, and automatically setting an average of distances between the IS/OS and the RPE calculated at a plurality of positions as the threshold value. Further, the IS/OS may be segmented from a polarization-sensitive tomographic image to determine whether the protrusion contacts (or intersects) the IS/OS.

<Output>

Next, step S105 will be described as processing for outputting each generated image and an analysis result. In the output processing according to the present exemplary embodiment, the map K acquired in step S104 is displayed so as to allow the user to easily understand the result.

After the image generation unit 193 and the image analysis unit 194 in the signal processing unit 190 complete the generation and analysis of each image, the display control unit 191 generates output information based on this result, and outputs the generated information to the display unit 192 to be displayed.

Figure 10:
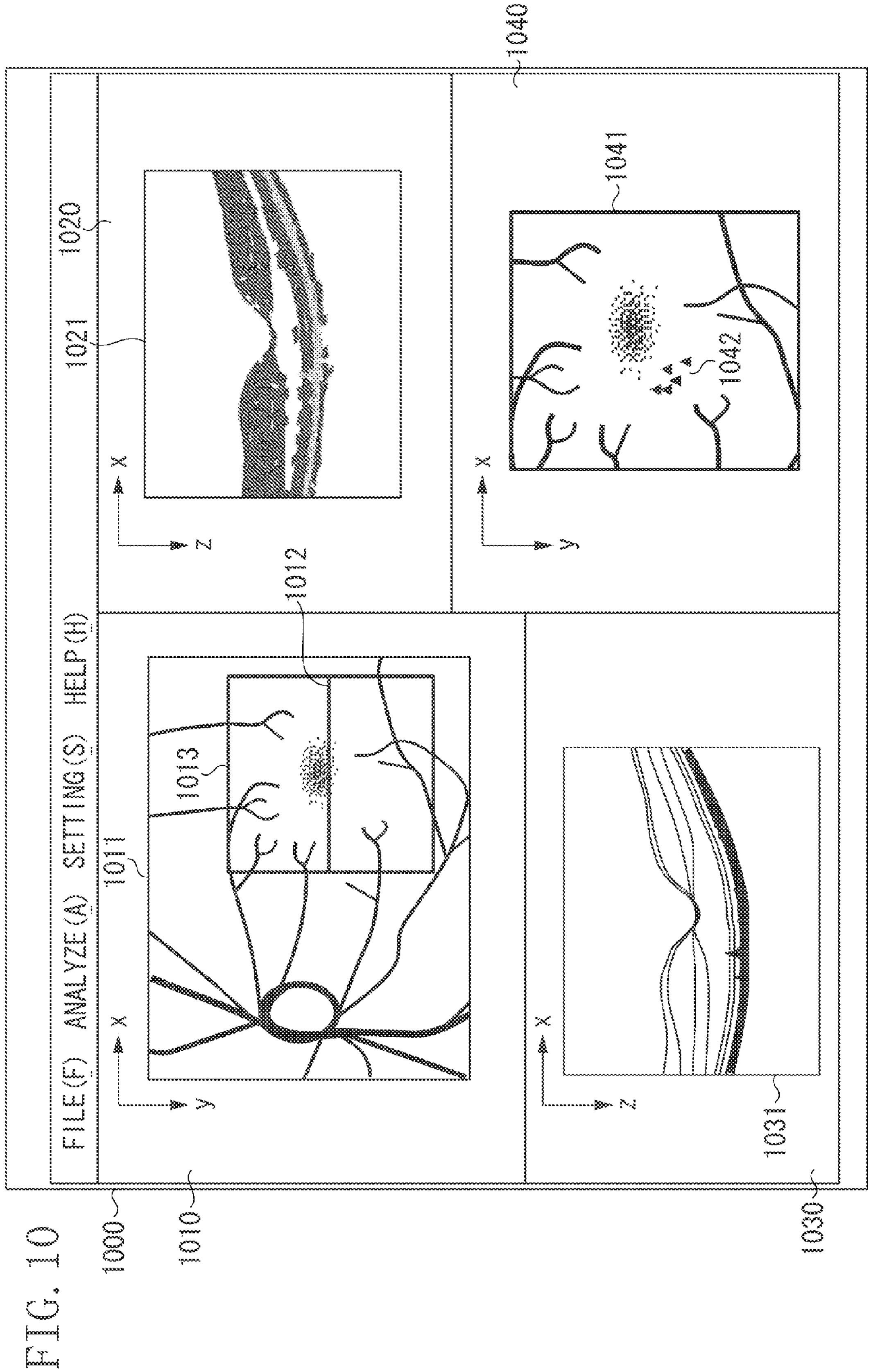
FIG. 10 illustrates a display form that indicates a result of analysis according to the exemplary embodiment of the present invention.

FIG. 10 is an example of the display on the display unit 192 according to the present exemplary embodiment. In FIG. 10, a window 1000 displayed on the display unit 192 includes display areas 1010, 1020, 1030, and 1040.

In the display area 1010, a rectangular frame 1013, which indicates a photographed position in a tomographic image, and an indication 1012, which indicates a position of a tomographic image 1021, are superimposed on a fundus image 1011. The fundus image 1011 is photographed by the PS-SLO 140. The tomographic image 1021 at the position indicated by the indication 1012 is displayed in the display area 1020. In FIG. 10, this tomographic image is a DOPU image, but may be another tomographic image such as a luminance image.

Further, a tomographic image 1031 is displayed in the display area 1030. The tomographic image 1031 is formed by superimposing the region where light is depolarized, which is extracted from the DOPU image, and the tomographic image resulting from layer extraction as described above. The tomographic image displayed in a superimposed manner may be another tomographic image such as a retardation image or a luminance image.

An image, which is formed by superimposing the map K indicating the position of the portion invading the IS/OS in the region where light is depolarized as illustrated in FIG. 9, and a fundus image, is displayed in the display area 1040. An indication 1042 indicates the position of the portion that reaches the IS/OS in the region where light is depolarized. The fundus image displayed here corresponds to the region surrounded by the rectangular frame 1013 in the fundus image 1011. This display enables the user to easily recognize where a region likely leading to visual disability is positioned on the fundus. In addition to displaying the position of the invading portion, the degree of the invasion may be displayed with, for example, a color map. The degree of the invasion means a value such as a thickness and an area acquired by quantifying the invading portion.

In this manner, it is possible to display, on the display unit 192, a portion invading a predetermined layer (for example, a layer having the visual function) of a subject in a region where light is depolarized, which is extracted from a tomographic image indicating a polarization state of the subject. As a result, it is possible to effectively present a portion that may affect the visual function of the subject's eye in the region extracted from the polarization-sensitive OCT image, to the user.

The superimposed fundus image in the present exemplary embodiment does not necessarily have to be limited to an image captured by the PS-SLO 140, and may be a pseudo SLO image generated by integral projection from a tomographic luminance image. In this case, the image analysis unit 194 performs integral projection on a series of tomographic images illustrated in FIG. 5 in a Z direction to generate a pseudo SLO image having M pixels and N pixels in the horizontal and vertical directions, respectively, and displays the indication 1402 on the pseudo SLO image in a superimposed manner.

Another Embodiment

Further, the present invention can be also carried out by performing the following procedure. The procedure is supplying software (a program) capable of realizing the functions of the above-described exemplary embodiment to a system or an apparatus via a network or various kinds of storage media, and causing a computer (or, for example, a central processing unit (CPU) or a micro processing unit (MPU)) of the system or the apparatus to read out and execute the program.

According to the present invention, it is possible to display, on the display unit, a portion invading a predetermined layer (for example, a layer having the visual function) of a subject in a region where light is depolarized, which is extracted from a polarization-sensitive tomographic image of the subject. As a result, it is possible to effectively present a portion that may affect the visual function of the subject's eye in the region extracted from the polarization-sensitive OCT image, to the user.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-239274 filed Oct. 30, 2012 and No. 2013-159181 filed Jul. 31, 2013, which are hereby incorporated by reference herein in their entirety.

What is claimed is:

1. An image processing apparatus comprising:

a tomographic image acquisition unit configured to acquire a polarization-sensitive tomographic image of a subject and a tomographic luminance image of the subject;

an extraction unit configured to extract a depolarizing region in the polarization-sensitive tomographic image and to extract a layer having a visual function in the tomographic luminance image;

a determination unit configured to determine a region which reaches the extracted layer in the extracted depolarizing region; and a display control unit configured to cause a display unit to display a region determined by the determination unit as the region which reaches the extracted layer.

2. The image processing apparatus according to claim 1, wherein the display control unit causes the display unit to display the region which reaches the extracted layer in a state of being superimposed on a corresponding position in a planar image of the subject.

3. The image processing apparatus according to claim 1, wherein the display control unit causes the display unit to display the extracted depolarizing region in a state of being superimposed on the extracted layer in the tomographic luminance image, and causes the display unit to display the region which reaches the extracted layer in a state of being superimposed on the tomographic luminance image.

4. The image processing apparatus according to claim 1, wherein the determination unit determines that a region which is in contact with the extracted layer in the extracted depolarizing region.

5. The image processing apparatus according to claim 1, wherein the determination unit determines a region located at a position corresponding to a threshold value or a larger value from the extracted layer in a depth direction is the region which reaches the extracted layer, in extracted depolarizing region.

6. The image processing apparatus according to claim 1, wherein the image processing apparatus is connectable with an imaging apparatus, the imaging apparatus includes a detecting unit configured to detect different polarized light beams, which are acquired by dividing combined light of light returning from the subject illuminated with measurement light and reference light corresponding to the measurement light, and wherein the tomographic image acquisition unit acquires the polarization-sensitive tomographic image and the tomographic luminance image based on the detected different polarized light beams.

7. An image processing apparatus comprising:

a tomographic image acquisition unit configured to acquire a polarization-sensitive tomographic image of a subject and a tomographic luminance image of the subject;

an extraction unit configured to extract a predetermined region in the polarization-sensitive tomographic image and extract a layer having a visual function in the tomographic luminance image; and a determination unit configured to determine a region which reaches the extracted layer.

8. The image processing apparatus according to claim 7, further comprising a display control unit configured to cause the display unit to display the region which reaches the extracted layer.

9. The image processing apparatus according to claim 7, further comprising:

a unit configured to quantify the region which reaches the extracted layer.

10. The image processing apparatus according to claim 7, wherein the subject is a subject's eye, wherein a part of the predetermined region is a RPE layer of a fundus of the subject's eye, and wherein the layer having the visual function is IS/OS.

11. An image processing method comprising:

acquiring a polarization-sensitive tomographic image of a subject and a tomographic luminance image of the subject;

extracting a depolarizing region in the polarization-sensitive tomographic image and extracting a layer having a visual function in the tomographic luminance image;

determining a region which reaches the extracted layer in the extracted depolarizing region; and causing a display unit to display a region determined by the determining as the region which reaches the extracted layer.

12. The image processing method according to claim 11, wherein the region which reaches the extracted layer is displayed on the display unit in a state of being superimposed on a corresponding position in a planar image of the subject.

13. The image processing method according to claim 11, wherein the extracted depolarizing region is displayed on the display unit in a state of being superimposed on the extracted layer in tomographic luminance image, and the region which reaches the extracted layer is displayed on the display unit in a state of being superimposed on the tomographic luminance image.

14. The image processing method according to claim 11, wherein a region which is in contact with the extracted layer in the extracted depolarizing region is determined.

15. The image processing method according to claim 11, wherein a region located at a position corresponding to a threshold value or a larger value from the extracted layer in a depth direction in the extracted depolarizing region is determined.

16. The image processing apparatus according to claim 7, wherein the image processing apparatus is connectable with an imaging apparatus, the imaging apparatus includes a detecting unit configured to detect different polarized light beams, which are acquired by dividing combined light of light returning from the subject illuminated with measurement light and reference light corresponding to the measurement light, and wherein the tomographic image acquisition unit acquires the polarization-sensitive tomographic image and the tomographic luminance image based on the detected different polarized light beams.

17. An image processing method comprising:

acquiring a polarization-sensitive tomographic image of a subject and a tomographic luminance image of the subject;

extracting a predetermined region in the polarization-sensitive tomographic image and extracting a layer having a visual function in the tomographic luminance image; and determining a region which reaches the extracted layer.

18. A non-transitory computer-readable storage medium storing a program for causing a computer to execute the image processing method according to claim 11.

19. A non-transitory computer-readable storage medium storing a program for causing a computer to execute the image processing method according to claim 17.

* * * * *